United States Patent [19]

Molt et al.

[11] 4,305,839

[45] Dec. 15, 1981

[54] HYDROXYBENZOPHENONES

[75] Inventors: Kenneth R. Molt; Thomas G. Kugele, both of Cincinnati; Karl R. Wursthorn, Fairfield, all of Ohio

[73] Assignee: Carstab Corporation, Reading, Ohio

[21] Appl. No.: 954,998

[22] Filed: Oct. 26, 1978

[51] Int. Cl.$^3$ .............................................. C09K 3/00
[52] U.S. Cl. ............................................. 252/400 A
[58] Field of Search ........................... 260/590 D, 23; 252/400 A

[56] References Cited

U.S. PATENT DOCUMENTS 2,951,052 8/1960 Darby .................................. 260/23
3,658,910 4/1972 Hechenbleikner ................. 260/591

Primary Examiner—Brooks H. Hunt
Assistant Examiner—J. L. Barr
Attorney, Agent, or Firm—Richard J. Sheridan

[57] ABSTRACT

The storage stability of impure hydroxybenzophenones is improved by the addition thereto of an organic phosphite or organic phosphonite.

11 Claims, No Drawings

HYDROXYBENZOPHENONES

FIELD OF INVENTION

This invention relates to hydroxybenzophenones useful as stabilizers for organic polymers. Particularly this invention relates to hydroxybenzophenones having improved storage stability. More particularly this invention relates to combinations of an impure hydroxybenzophenone and an organic phosphite or organic phosphonite compound.

BACKGROUND

Hydroxybenzophenones have been known in the art for quite sometime, particularly with respect to their utility as stabilizers for organic polymers. More particularly substituted and unsubstituted 2-hydroxybenzophenones have been widely used as UV stabilizers for polyolefins. Thus they are of significant commercial interest. The manufacture of substituted and unsubstituted 2-hydroxybenzophenones, particularly by commercial processes, yields products which very often contain impurities. These impurities contribute color to the product and/or cause the product to be color unstable upon standing, particularly when exposed to light and air. Color changes and/or darkening sometimes occur in a matter of a few hours at room temperature. Such color changes, which are often caused by a small percentage of impurity which is difficult to remove, reduce the commercial acceptance of such substituted or unsubstituted 2-hydroxybenzophenones and thereby impedes the commercial use of these materials. To, at least in part, overcome these color and color instability problems the prior art resorted to physical means to highly purify the impure substituted and unsubstituted hydroxybenzophenones. These physical means have added steps and cost to the preparation of the 2-hydroxybenzophenones and in some cases caused decreased yields.

Since hydroxybenzophenones are valuable UV stabilizers in commerce, it is highly desirable to overcome these color and color instability problems, particularly without burdening the process and significantly increasing the cost of making them.

SUMMARY OF THE INVENTION

It is an object of this invention to overcome the color instability of impure hydroxybenzophenones.

Another object of this invention is to provide color stable substituted and unsubstituted hydroxybenzophenones.

A still further object of this invention is to provide a method for stabilizing substituted and unsubstituted hydroxybenzophenones against color change upon standing.

Other objects of this invention will become apparent from the following description.

It has now been found that the above objects and others can be realized by a polymer free composition comprising a substituted or unsubstituted 2-hydroxybenzophenone and an organic phosphorus compound selected from the group consisting of secondary organic phosphite, tertiary organic phosphite or organic phosphonite. Further, there has now been found a method of stabilizing substituted and unsubstituted 2-hydroxybenzophenones against color change during storage comprising the step of adding to said 2-hydroxybenzophenone a secondary organic phosphite or a tertiary organic phosphite or an organic phosphonite.

DESCRIPTION OF THE INVENTION

In accordance with this invention there are provided polymer free substituted and unsubstituted 2-hydroxybenzophenone compositions, resistant to color change upon standing, comprising a color unstable substituted or unsubstituted 2-hydroxybenzophenone, and an organic phosphorus compound selected from the group consisting of secondary organic phosphite, tertiary organic phosphite or an organic phosphonite. The substituted and unsubstituted 2-hydroxybenzophenones in accordance with this invention can be given by the following formula.

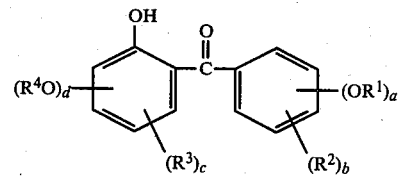

wherein:
$R^1$ and $R^4$ are the same or different and are selected from the group consisting of (1) hydrogen and (2) unsubstituted and substituted alkyl, aryl, alkaryl, aralkyl, alkenyl or cycloalkyl group wherein the substituent is halogen,
$R^2$ and $R^3$ are the same or different and are selected from the group consisting of $R^1$, Br, Cl and alkoxy,
a is 0, 1 or 2,
b is 0, 1 or 2,
c is 0, 1 or 2
d is 0, 1 or 2,
a+b is 0 to 3,
c+d is 0 to 3 and
a+b+c+d is 0 to 4.

Secondary and tertiary organic phosphites according to this invention are organic phosphites having a trivalent phosphorus atom and two or three P-O-C linkages (i.e. phosphorus-oxygen-carbon linkage) which may, for example, be described by the formulae

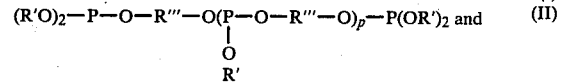

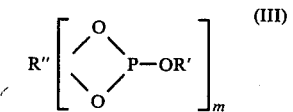

wherein R is hydrogen, an aliphatic (preferably $C_8$ to $C_{20}$ alkyl), aromatic (preferably phenyl), alkyl substituted aromatic (preferably $C_7$ to $C_{18}$), aryl substituted aliphatic (preferably $C_7$ to $C_{18}$), cycloaliphatic (preferably $C_6$), diphenyl or phenyl-alkylene-phenyl group having a valence equal to n, R' an alkyl (preferably $C_8$ to $C_{20}$), hydroxyalkyl, aryl (preferably phenyl), aralkyl (preferably $C_7$ to $C_{18}$), alkaryl (preferably $C_7$ to $C_{18}$), alkenyl or cycloalkyl (preferably $C_6$) group, or R' groups and optionally the R group together with the oxygen atoms and phosphorus atom of the phosphite join to form a heterocyclic ring structure, R" is a divalent or tetravalent aliphatic, aromatic or cycloaliphatic radical, R''' is an alkylene group optionally containing ether linkages, m is 1 or 2, n is an integer from 1 to 6 and p is an integer from 1 to 1000. The organic phosphonites according to this invention may be, for example, described by the formulae

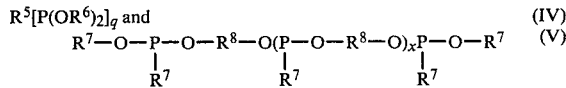

wherein $R^5$ is hydrogen, or an aliphatic, aromatic, alkyl substituted aromatic, aryl substituted aliphatic or cycloaliphatic radical having a valence of q, $R^6$ is an alkyl, aryl, aralkyl, alkaryl, cycloalkyl or alkenyl group or the $R^6$ groups together with the oxygen atoms and the phosphorus atom may join to form a heterocyclic ring, $R^7$ is an alkyl, aryl, aralkyl, alkaryl, cycloalkyl or alkenyl group, $R^8$ is an alkylene group optionally containing ether linkages, q is an integer from 1 to 6 and x is an integer from 1 to 1000. The preferred secondary organic phosphites, tertiary organic phosphites and organic phosphonites usable in this invention are those having low volatility, especially at elevated temperatures.

This invention provides useful improved polymer free 2-hydroxybenzophenone compositions which are resistant to color change on standing, particularly upon standing exposed to light and air. As one embodiment of this invention there is provided a polymer free 2-hydroxybenzophenone composition comprising (a) a substituted or unsubstituted 2-hydroxybenzophenone which is color unstable upon standing and (b) a secondary or tertiary organic phosphite. According to another embodiment of this invention, there is provided a polymer free 2-hydroxybenzophenone composition comprising (a) a substituted or unsubstituted 2-hydroxybenzophenone which is color unstable upon standing and (b) an organic phosphonite. In a further embodiment of this invention polymer free 2-hydroxybenzophenone compositions are provided comprising (a) a substituted or unsubstituted 2-hydroxybenzophenone which is color unstable upon standing and (b) an organic phosphite according to formula (I) above. Other embodiments of this invention include polymer free 2-hydroxybenzophenone compositions comprising a substituted or unsubstituted 2-hydroxybenzophenone which is color unstable upon standing and an organic phosphite according to formula II or III above or an organic phosphonite according to formula IV or V above.

The polymer free 2-hydroxybenzophenone compositions of this invention are useful as stabilizers (e.g. heat and light stabilizers for polyolefins (e.g. polyethylene and polypropylene or their copolymers). In the context of this disclosure and of the claims of this invention the phrase polymer free 2-hydroxybenzophenone compositions shall mean 2-hydroxybenzophenone compositions of this invention which do not contain a polymer for which substituted and unsubstituted 2-hydroxybenzophenones and/or secondary organic phosphites, tertiary organic phosphites and organic phosphonites are stabilizers.

In the practice of this invention the secondary organic phosphite, tertiary organic phosphite or the organic phosphonite may be combined with the 2-hydroxybenzophenone over a wide concentration range. Thus, for example, as little as 0.01 part and as high as 90 parts of the secondary organic phosphite, tertiary organic phosphite or the organic phosphonite may be present in 100 parts total of the combination of the substituted or unsubstituted 2-hydroxybenzophenone and the secondary organic phosphite or tertiary organic phosphite or the organic phosphonite. The amount of the secondary organic phosphite, tertiary organic phosphite or the organic phosphonite present in the mixture will depend on a number factors including the composition of the substituted or unsubstituted 2-hydroxybenzophenone, the color instability of the substituted or unsubstituted 2-hydroxybenzophenone, the nature of the secondary organic phosphite, tertiary organic phosphite or the organic phosphonite, the intended use of the combination, compatibility and costs. Preferably, the amount of the secondary organic phosphite, tertiary organic phosphite or organic phosphonite in the compositions of this invention ranges from about 0.1 to about 25 percent, more preferably from about 0.5 to about 10 percent, based on the total weight of the combination of the secondary organic phosphite or tertiary organic phosphite or the organic phosphonite and the substituted or unsubstituted 2-hydroxybenzophenone. The organic phosphites are preferred, tertiary organic phosphites more preferred and aliphatic tertiary organic phosphites still more preferred in the practice of this invention. Combinations of color unstable unsubstituted or substituted 2-hydroxybenzophenone and an aliphatic tertiary organic phosphite having 8 to 18 carbon atoms in the aliphatic group are especially preferred.

Substituted and unsubstituted 2-hydroxybenzophenones usable in the practice of this invention include, but are not limited to, color unstable:
2-hydroxybenzophenone
2-hydroxy-4-methoxybenzophenone
2-hydroxy-4-hexyloxybenzophenone
2-hydroxy-4-heptyloxybenzophenone
2-hydroxy-4-octyloxybenzophenone
2-hydroxy-4-(2-ethyhexyloxy)benzophenone
2-hydroxy-4-benzyloxybenzophenone
2-hydroxy-4-octadecyloxybenzophenone
2-hydroxy-4-methylbenzophenone
2-hydroxy-4-decylbenzophenone
2-hydroxy-4-bromobenzophenone
2-hydroxy-4-chlorobenzophenone
2-hydroxy-4-iodobenzophenone
2-hydroxy-4-methoxy-4'-tertiary butylbenzophenone
2-hydroxy-4-benzyloxy-4'-octylbenzophenone
2-hydroxy-4-decyloxy-4'-butylbenzophenone
2-hydroxy-4-(pentachlorobenzoyloxy) benzophenone
2-hydroxy-4-octylbenzophenone
2-hydroxy-4-isooctylbenzophenone
2-hydroxy-4-isooctyloxybenzophenone
2-hydroxy-4,4'-dimethoxybenzophenone
2-hydroxy-4,4'-dimethylbenzophenone
2-hydroxy-4,5-dimethylbenzophenone
2-hydroxy-4-ethyl-3'-chlorobenzophenone
2-hydroxy-4-methoxy-4'-octoxybenzophenone
2,2'-dihydroxybenzophenone
2,2'-dihydroxy-4-methylbenzophenone
2,2'-dihydroxy-4'-tertiary butylbenzophenone
2,2'-dihydroxy-4,4'-dimethoxybenzophenone
2,2'-dihydroxy-4-octoxybenzophenone
2,2'-dihydroxy-4-isooctoxybenzophenone
2,2'-dihydroxy-4-benzoxybenzophenone
2,2'-dihydroxy-4-octoxy-4'-methoxybenzophenone
2,2'-dihydroxy-4-4'-dioctoxybenzophenone
2,2'-dihydroxy-4-chlorobenzophenone
2,4-dihydroxybenzophenone 2,2',4-trihydroxybenzophenone As secondary and tertiary organic phosphites usable in the practice of this invention there includes, but not limited to, for example:
triphenyl phosphite
tricyclohexyl phosphite
triethyl phosphite
trioctyl phosphite
trihexyl phosphite
tridodecyl phosphite
trioctadecyl phosphite
triisopropyl phosphite
tri-tertiary butyl phosphite
tri 2-ethylhexyl phosphite
tricresyl phosphite
tri (dimethylphenyl)phosphite
tri (t-octylphenyl) phosphite
tri (nonylphenyl) phosphite
tri docosanyl phosphite
monophenyl dioctyl phosphite
tri benzyl phosphite
monobutyl-diphenyl phosphite
mono-nonylphenyl-dioctyl phosphite
monohexyl diisopropyl phosphite
cycohexyl-dioctadecyl phosphite
diphenyl-neopentyl diphosphite
diisooctyl-octylphenyl phosphite
tetrakis (nonylphenyl) propylene glycol diphosphite
heptakis (dipropylene glycol) triphosphite
poly (dipropylene glycol) phenyl phosphite
distearyl pentaerythritol diphosphite
neopentyl diphosphite
dilauryl hydrogen phosphite
dioctyl hydrogen phosphite
dioctadecyl hydrogen phosphite
trimethylol propane phosphite
2,2-dimethyl-1,3-propylene lauryl phosphite Illustrative of the organic phosphonites that may be used in the practice of this invention are alkyl, aryl, aralkyl, alkaryl, cycloalkyl and heterocyclic phosphonites—examples of which include, but are not limited to,
phenyl diethyl phosphonite
octyl dibutyl phosphonite
decyl diisopropyl phosphonite
hexyl di-tertiary butyl phosphonite
dodecyl dioctyl phosphonite
cyclohexyl dioctadecyl phosphonite
lauryl diphenyl phosphonite
phenyl dicyclohexyl phosphonite
nonylphenyl di-nonylphenyl phosphonite
stearyl di-benzyl phosphonite
dioctyl neopentyl diphosphonite Organic phosphonites also usable in the practice of this invention include those phosphonites disclosed in U.S. Pat. Nos. 3,928,510, 3,962,175 and 3,978,020 the entire disclosures of which are incorporated herein by reference.

Methods well known in the art may be used to make the combination of the color unstable substituted or unsubstituted 2-hydroxybenzophenone and the secondary organic phosphite or tertiary organic phosphite or the organic phosphonite according to this invention.

TABLE I

| Example | Phosphite | Percent | Percent Before | Transmission After |
|---|---|---|---|---|
| 1 | none | 0 | 81.3 | 22.8 |
| 2 | trilauryl phosphite | 0.5 | 82.0 | 64.3 |
| 3 | " | 5.0 | 85.1 | 85.9 |
| 4 | " | 25.0 | 94.3 | 95.0 |
| 5 | " | 50.0 | 98.4 | 98.2 |
| 6 | phenyldidecyl phosphite | 5.0 | 83.6 | 80.9 |
| 7 | phenyldidecyl phosphite | 25.0 | 92.8 | 93.1 |
| 8 | neopentyl diphosphite | 5.0 | 84.0 | 83.9 |
| 9 | triphenyl phosphite | 5.0 | 81.6 | 52.0 |
| 10 | tris-nonylphenyl phosphite | 5.0 | 80.9 | 55.8 |
| 11 | diphenyldecyl phosphite | 5.0 | 82.3 | 74.1 |
| 12 | tricyclohexyl phosphite | 5.0 | 81.9 | 80.0 |
| 13 | tributyl phosphite | 5.0 | 83.3 | 82.9 |
| 14 | trioctadecyl phosphite | 5.0 | 82.6 | 83.3 |
| 15 | " | 0.5 | 80.3 | 61.1 |
| 16 | " | 25.0 | 92.1 | 91.4 |
| 17 | " | 70.0 | 99.1 | 99.3 |
| 18 | tridocosanyl phosphite | 5.0 | 83.1 | 82.6 |
| 19 | phenylneopentyl phosphite | 5.0 | 80.9 | 76.6 |
| 20 | diisooctyloctylphenyl phosphite | 5.0 | 81.7 | 73.4 |
| 21 | tetrakis(nonylphenyl) propyleneglycol diphosphite | 5.0 | 82.3 | 74.0 |
| 22 | heptakis(dipropyleneglycol)- triphosphite | 5.0 | 83.0 | 79.9 |
| 23 | poly(dipropyleneglycol) phenyl phosphite | 5.0 | 81.1 | 78.8 |

Thus the color unstable substituted or unsubstituted 2-hydroxybenzophenone may be mixed with the secondary or tertiary organic phosphite or organic phosphonite or conversely the secondary or tertiary organic phosphite or organic phosphonite may be mixed with the color unstable substituted or unsubstituted 2-hydroxybenzophenone at reduced, room or elevated temperatures by wet or dry techniques using mixers well known in the art. Solvents may be employed in making the combinations.

This invention is further described with respect to specific embodiments by the following non-limiting examples.

EXAMPLES 1–29

Test mixtures of 2-hydroxy-4-isooctoxybenzophenone with various phosphites or a phosphonite were placed in 2 oz. square bottles (clear glass) and exposed to indirect sunlight for 5 days. The color was measured before and after exposure by diluting a portion of the mixture with toluene (90% toluene, 10% test mixture) and measuring the transmission at 480 mu on a Coleman Spectrophotometer (Model 44). The test results using several different phosphites and one phosphonite are shown in Table I.

| Example | Phosphite | Percent | Percent Before | Transmission After |
|---|---|---|---|---|
| 24 | distearylpentaerythritol diphosphite | 5.0 | 82.9 | 84.6 |
| 25 | distearylpentaerythritol diphosphite | 0.5 | 81.3 | 66.1 |
| 26 | distearylpentaerythritol diphosphite | 10.0 | 87.1 | 88.0 |
| 27 | phosphonite P-EPQ** | 5.0 | 84.2 | 72.3 |
| 28 | dilauryl phosphite | 25.0 | 93.8 | 94.1 |
| 29 | distearyl phosphite | 25.0 | 93.9 | 93.8 |

| Example | Phosphite | Percent | Percent Before | Transmission After |
|---|---|---|---|---|
| 30 | dioctyl phosphite | 25.0 | 92.7 | 95.1 |

**Sold by Sandox Colors & Chemicals of Hanover, New Jersey, and has the following structure:

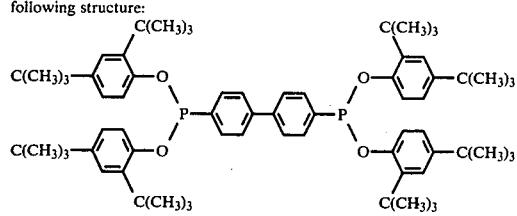

Although this invention has been described with respect to various embodiments, it is to be recognized that one skilled in the art may, from the above teachings, practice further embodiments without departing from the spirit and scope of the invention described above and claimed in the following claims.

We claim:

1. A polymer free composition comprising a color unstable substituted or unsubstituted 2-hydroxybenzophenone and a phorsphorus containing compound selected from the group consisting of organic phosphite and organic phosphonite wherein the substituted and unsubstituted 2-hydroxybenzophenone is given by the following formula.

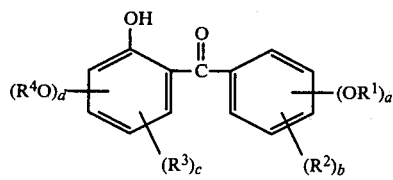

wherein:
R$^1$ and R$^4$ are the same or different and are selected from the group consisting of (1) hydrogen and (2) unsubstituted and substituted alkyl, aryl, alkaryl, aralkyl, alkenyl or cycloalkyl group wherein the substitutent is halogen,
R$^2$ and R$^3$ are the same or different and are selected from the group consisting of R$^1$, Br, Cl and alkoxy,
a is 0, 1 or 2,
b is 0, 1 or 2
c is 0, 1 or 2
d is 0, 1 or 2
a+b is 0 to 3
c+d is 0 to 3 and
a+b+c+d is 0 to 4 and
wherein the organic phosphite is described by the formulae

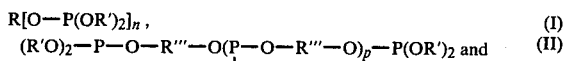

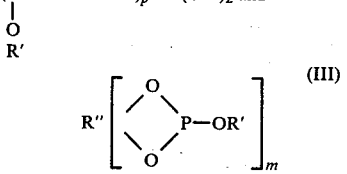

wherein R is an aliphatic, aromatic, alkyl substituted aromatic, aryl substituted aliphatic, cycloaliphatic, di-phenyl or phenyl-alkylene-phenyl group having a valence equal to n, R' is an alkyl, hydroxyalkyl, aryl, aralkyl, alkaryl, alkenyl or cycloalkyl group, R" is a divalent or tetravalent aliphatic, aromatic or cycloaliphatic radical, R''' is an alkylene group optionally containing ether linkages, m is 1 or 2, n is an integer from 2 to 6 and p is an integer from 1 to 1000 and the organic phosphonite is described by the formulae

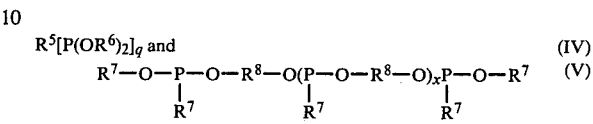

wherein R$^5$ is hydrogen, or an aliphatic, aromatic, alkyl substituted aromatic, aryl substituted aliphatic or cycloaliphatic radical having a valence of q, R$^6$ is an alkyl, aryl, aralkyl, alkaryl, cycloalkyl or alkenyl group or the R$^6$ groups together with the oxygen atoms and the phosphorus atom may join to form a heterocyclic ring, R$^7$ is an alkyl, aryl, aralkyl, alkaryl, cycloalkyl or alkenyl group, R$^8$ is an alkylene group optionally containing ether linkages, q is an integer from 1 to 6 and x is an integer from 1 to 1000.

2. A method of stabilizing substituted and unsubstituted 2-hydroxybenzophenones against color change comprising the step of adding to a color unstable substituted or unsubstituted 2-hydroxybenzophenone a color stabilizing amount of a phosphorus containing compound selected from the group consisting of organic phosphite and organic phosphonite wherein the substituted and unsubstituted 2-hydroxybenzophenone is given by the following formula.

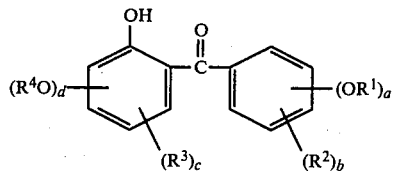

wherein
R$^1$ and R$^4$ are the same or different and are selected from the group consisting of (1) hydrogen and (2) substituted and unsubstituted alkyl, aryl, alkaryl, aralkyl, alkenyl or cycloalkyl group wherein the substitutent is halogen,
R$^2$ and R$^3$ are the same or different and are selected from the group consisting of R$^1$, Br, Cl and alkoxy,
a is 0, 1 or 2,
b is 0, 1 or 2,
c is 0, 1 or 2,
d is 0, 1 or 2,
a+b is 0 to 3
c+d is 0 to 3 and
a+b+c+d is 0 to 4 and
wherein the organic phosphite is described by the formulae

-continued

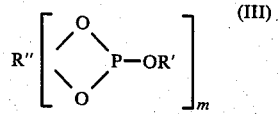

wherein R is an aliphatic, aromatic, alkyl substituted aromatic, aryl substituted aliphatic, cycloaliphatic, diphenyl or phenyl-alkylene-phenyl group having a valence equal to n, R' is an alkyl, hydroxyalkyl, aryl, aralkyl, alkaryl, alkenyl or cycloalkyl, R" is a divalent or tetravalent aliphatic, aromatic or cycloaliphatic radical, R''' is an alkylene group optionally containing ether linkages, m is 1 or 2, n is an integer from 2 to 6 and p is an integer from 1 to 1000 and the organic phosphonite is described by the formulae

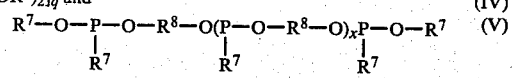

wherein $R^5$ is hydrogen, or an aliphatic, aromatic, alkyl substituted aromatic, aryl substituted aliphatic or cycloaliphatic radical having a valence of q, $R^6$ is an alkyl, aryl, aralkyl, alkaryl, cycloalkyl or alkenyl group or the $R^6$ groups together with the oxygen atoms and the phosphorus atom may join to form a heterocyclic ring, $R^7$ is an alkyl, aryl, aralkyl, alkaryl, cycloalkyl or alkenyl group, $R^8$ is an alkylene group optionally containing ether linkages, q is an integer from 1 to 6 and x is an integer from 1 to 1000.

3. A composition according to claim 1 wherein the phosphorus containing compound is an organic phosphite.

4. A composition according to claim 1 wherein the phosphorus containing compound is an organic phosphonite.

5. A composition according to claim 3 wherein the tertiary organic phosphite is a trialkyl phosphite according to formula (I).

6. A composition according to claim 3 wherein the tertiary organic phosphite is a tri aralkyl phosphite according to formula (I).

7. A composition according to claim 3 wherein the tertiary organic phosphite is a tri cycloalkyl phosphite according to formula (I).

8. A composition according to claim 1 wherein the phosphorus containing compound is present in an amount of from 0.5 to 50 weight percent based on the combined weight of the hydroxybenzophenone and the phosphorus containing compound.

9. A composition according to claim 8 wherein the phosphorus containing compound is present in an amount of from 0.5 to 10 weight percent.

10. The method according to claim 2 wherein the phosphorus containing compound is a tertiary organic phosphite.

11. The method according to claim 2 wherein the phosphorus containing compound is an organic phosphonite.

* * * * *